United States Patent [19]

Connor

[11] 4,287,126
[45] Sep. 1, 1981

[54] (2-OXO-2H-1-BENZOPYRAN-3-YL)AMINOOXOACETIC ACIDS AND THEIR DERIVATIVES

[75] Inventor: David T. Connor, Ann Arbor, Mich.
[73] Assignee: Warner-Lambert Company, Morris Plains, N.J.
[21] Appl. No.: 128,760
[22] Filed: Mar. 10, 1980
[51] Int. Cl.³ .................. C07D 311/12; C07D 311/08
[52] U.S. Cl. ............................... 260/343.45; 424/281
[58] Field of Search .................................... 260/343.45

[56] References Cited
U.S. PATENT DOCUMENTS 3,008,969  11/1961  Pretka ............................ 260/343.45
4,205,082  5/1980  Ferrini ............................ 260/343.45

Primary Examiner—Henry R. Jiles
Assistant Examiner—Jane T. Fan
Attorney, Agent, or Firm—Stephen Raines

[57] ABSTRACT

The present invention relates to (2-oxo-2H-1-benzopyran-3-yl)aminooxoacetic acids and their derivatives having the following structural formula:

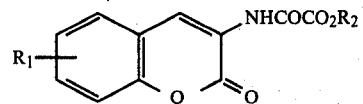

wherein $R_1$ is hydrogen, halogen, hydroxy, lower alkoxy, lower alkyl or nitro and $R_2$ is hydrogen or lower alkyl and their pharmaceutically acceptable salts thereof; these compounds are indicated in the management of allergic manifestations such as, for example, asthma, hay fever and the like.

The present invention relates to (2-oxo-2H-1-benzopyran-3-yl)aminooxoacetic acids and their derivatives having the following structural formula:

wherein $R_1$ is hydrogen, halogen, hydroxy, lower alkoxy, lower alkyl or nitro. $R_2$ is hydrogen or lower alkyl and their pharmaceutically acceptable salts thereof.

11 Claims, No Drawings

(2-OXO-2H-1-BENZOPYRAN-3-YL)AMINOOXOACETIC ACIDS AND THEIR DERIVATIVES

In the above definitions for $R_1$ and $R_2$ the term "lower alkyl" and the alkyl portion of the term "lower alkoxy" embraces both straight and branched chain alkyl radicals having from 1 to 6 carbon atoms, for example; methyl, ethyl, propyl, isopropyl, n-butyl, n-amyl and the like. The term "halogen" embraces all its four members i.e. chlorine, bromine, fluorine and iodine.

The compounds of this invention, as well as their pharmaceutically acceptable salts, are active in the prevention of allergic reactions in mammals such as mice, rats and guinea pigs. Typically, using rats as the host, and employing the passive cutaneous anaphalaxis (PCA) test, which is described in *Life Sciences*, 7; 465 (1963), *Proc. Soc. Exptl. Biol. Med.*, 81; 585 (1952) and U.S. Pat. No. 3,076,720.

The compounds of this invention or their salts were effective in preventing allergic and asthmatic reactions in rats at dose levels of 0.5 mg/kg to 100 mg/kg. Typically, the compound (2-oxo-2H-1-benzopyran-3-yl)aminooxoacetic acid showed a 100% inhibition of the allergic response at 5 mg/kg when administered intraperitoneally in accordance with the aforedescribed test procedures.

The well known anti-allergic compound cromolyn sodium shows about 50% inhibition at 2 mg/kg intravenously in the PCA test.

The compounds in this invention including their salts are indicated in the management of mammals suffering from allergic manifestations such as bronchial asthma and hay fever. Generally speaking, a dose of 5 mg/kg to 100 mg/kg orally, parenterally, or by inhalation 1 to 3 times daily is suggested. As with any antiallergy therapy, the above dosage regiment must be titrated to individual needs by methods known to the healing arts.

According to a further feature of the present invention, there are provided pharmaceutical compositions which comprise as active ingredients, at least one of the compounds of this invention or their salts together with a pharmaceutical carrier. Thus, for example, solid compositions for oral administration include compressed tablets, pills, dispensable powders and granules. In such solid compositions, the selective active ingredient is mixed with at least one inert diluent such as calcium carbonate, calcium sulphate, or lactose. These compositions may also comprise, as known to the pharmacist art additional substances other than diluents, such as lubricating agents for example magnesium stearate. The resulting dosage forms such as tablets are prepared by methods known to the pharmacist art.

Liquid compositions for oral administration include for example, solutions, suspensions, syrups and elixirs containing inert diluents commonly used in the preparation of such dosage forms for example, water and simple syrup.

Preparations for parenteral administration include for example, sterile aqueous or non-aqueous solutions or suspensions. Examples of non-aqueous solvents or suspending media are for example, propylglycol, vegetable oils such as olive oil and injectable organic esters such as ethyl oleate.

According to the present invention, compound I in which $R_2$ is ethyl is prepared by reacting $R_1$-substituted 3-aminocoumarin of the formula:

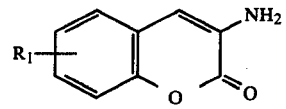

with ethyl oxalyl chloride of the formula:

         III in pyridine at ambient temperature. The resulting compound has the formula:

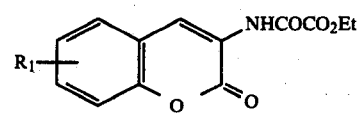

Compound IV, thus obtained is then treated with sodium hydroxide followed with treatment with hydrochloric acid to obtain those compounds of the invention in which $R_2$ is hydrogen.

The compounds of this invention in which $R_2$ is hydrogen can be readily alkylated to obtain other alkyl substituted compounds.

The pharmaceutically acceptable salts of Compound I are prepared by treating Compound I with a base such as sodium bicarbonate, sodium hydroxide, potassium bicarbonate, calcium bicarbonate or with organic bases.

The starting $R_1$ substituted aminocoumarins are prepared in accordance with the method of F. W. Lynch, *J. Chem. Soc.*, 101, 1758 (1912). This disclosure, as well as the disclosure in *Life Sciences, Proc. Soc. Exptl. Bio. Med.* and U.S. Pat. No. 4,076,720 referred to above, are incorporated herein by reference.

Briefly, the starting $R_1$ substituted aminocoumarins are prepared from $R_1$ substituted 2-hydroxy-benzaldehydes with glycine and sodium acetate in acetic anhydride at a temperature of about 120° for six hours. Examples 1 to 8 referred to hereinafter describe more fully the procedure for the preparation of this known compound.

In order to further illustrate the practice of this invention, the following examples in which temperature referred to therein are in degrees centigrade are included:

EXAMPLE 1

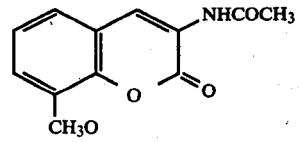

Acetamide, N-(8-methoxy-2-oxo-2H-1-benzopyran-3-yl)

A mixture of 2-hydroxy-3-methoxybenzaldehyde (15.2 g, 0.1 mole), glycine (7.5 g, 0.1 mole) and sodium acetate (10 g) in acetic anhydride (50 ml) is heated at 120° C. for 6 hours. The reaction mixture is cooled and triturated with water. The product is filtered off and washed with water. Recrystallization from ethanol gives white crystals (7.7 g, 33%) m.p. 237–239.

Anal. Calcd. for $C_{12}H_{11}NO_4$: C, 61.80; H, 4.75; N, 6.01. Found: C, 62.04; H, 4.85; N, 5.97.

EXAMPLE 2

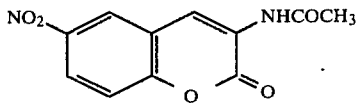

Acetamide, N-(6-nitro-2-oxo-2H-1-benzopyran-3-yl)

Prepared by the general method described for example 1 from 2-hydroxy-5-nitrobenzaldehyde (16.7 g, 0.1 mole). Recrystallization from butanol gives white crystals (14.4 g, 58%), mp. 250–255.

Anal. Calcd. for $C_{11}H_8N_2O_5$: C, 53.23; H, 3.25; N, 11.29. Found: C, 53.10; H, 3.20; N, 11.50.

EXAMPLE 3

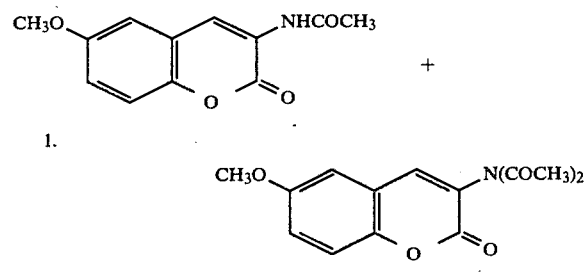

Acetamide,
N-(6-methoxy-2-oxo-2H-1-benzopyran-3-yl)-(1) and
Acetamide,
N-acetyl-N-(6-methoxy-2-oxo-2H-1-benzopyran-3-yl)-
(2)

A mixture of 2-hydroxy-5-methoxybenzaldehyde (4.5 g, 0.3 mole), glycine (22.5 g, 0.3 mole) and sodium acetate (30 g) in acetic anhydride (150 ml) is heated at 120° C. for 6 hours. The reaction mixture is cooled and triturated with water. The product is filtered off and washed with water. Recrystallization from ethanol gave 2 crops.

1. N-(6-methoxy-2-oxo-2H-1-benzopyran-3-yl)acetamide as yellow crystals (14 g, 20%) mp. 212–214

Anal. Calcd. for $C_{12}H_{11}NO_4$: C, 61.80; H, 4.75; N, 6.01. Found: C, 61.53; H, 4.71; N, 5.89.

2. N-acetyl-N-(6-methoxy-2-oxo-2H-1-benzopyran-3-yl)acetamide as yellow crystals (21 g, 25%) mp. 145–147.

Anal. Calcd. for $C_{14}H_{13}NO_5$: C, 61.09; H, 4.76; N, 5.09. Found: C, 60.85; H, 4.89; N, 5.10.

EXAMPLE 4

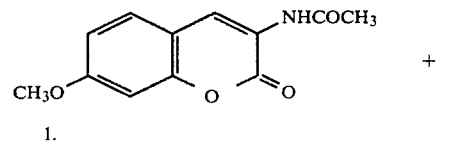

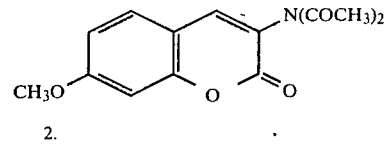

Acetamide,
N-(7-methoxy-2-oxo-2H-1-benzopyran-3-yl)-(1) and
Acetamide,
N-acetyl-N-(7-methoxy-2-oxo-2H-1-benzopyran-3-yl)-
(2)

Prepared by the general method described for example 3 from 2-hydroxy-4-methoxybenzaldehyde (50 g, 0.33 mole). Recrystallization from ethanol gives 2 crops.

1. N-(7-methoxy-2-oxo-2H-1-benzopyran-3-yl)acetamide as orange crystals (8.1 g, 11%), mp. 235–237.

Anal. Calcd. for $C_{12}H_{11}NO_4$: C, 61.80; H, 4.75; N, 6.01. Found: C, 61.50; H, 4.82; N, 6.06.

2. N-acetyl-N-(7-methoxy-2-oxo-2H-1-benzopyran-3-yl)acetamide as orange crystals (6.7 g, 7%) mp. 145–150.

Anal. Calcd. for $C_{14}H_{13}NO_5$: C, 61.09; H, 4.76; N, 5.09. Found: C, 61.02; H, 4.86; N, 5.32.

EXAMPLE 5

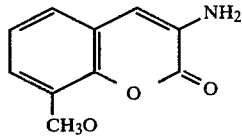

3-Amino-8-methoxycoumarin

N-(8-methoxy-2-oxo-2H-1-benzopyran-3-yl)acetamide (17 g; 0.073 mole) is suspended in concentrated hydrochloric acid (200 ml). The reaction mixture is heated at 100° C. for 1 hour and then cooled in an icebath. The product is filtered off, sucked dry and recrystallized from methanol to give off-white crystals (12 g, 86%) mp. 128–130.

Anal. Calcd. for $C_{10}H_9NO_3$: C, 62.82; H, 4.75; N, 7.33. Found: D, 62.66; H, 4.80; N, 7.10.

D. Chakrati and R. Das, *J. Indian Chem. Soc.* 48, 371–374 (1971)

EXAMPLE 6

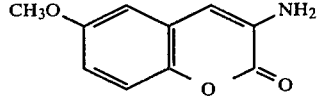

3-Amino-6-methoxycoumarin

N-(6-methoxy-2-oxo-2H-1-benzopyran-3yl)acetamide (12.5 g) is slowly suspended in concentrated hydrochloric acid (300 ml). The reaction mixture is heated at 100° C. for 40 minutes then cooled in an ice-bath. The product is filtered off, sucked dry and recrystallized from methanol to give brown crystals (4.2 g, 48%), mp. 120–123.

Anal. Calcd. for C₁₀H₉NO₃: C, 62.82; H, 4.75; N, 7.33. Found: C, 62.47; H, 4.95; N, 7.34.

G. Domschke, Z. Chem 2, 114 (1962)

EXAMPLE 7

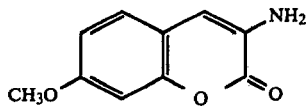

3-Amino-7-methoxycoumarin

Prepared by the method described for example 6 from N-(7-methoxy-2-oxo-2H-1-benzopyran-3-yl)acetamide (9.0 g, 0.038 mole). The product is recrystallized from methanol to give brown crystals (6.5 g, 88%), mp. 153–155.

Anal. Calcd. for C₁₀H₉NO₃: C, 62.82; H, 4.75; N, 7.33. Found: C, 62.27; H, 4.80; N, 7.03.

D. Chakrati and R. Das, *J. Indian Chem. Soc.* 48, 371–374 (1971)

EXAMPLE 8

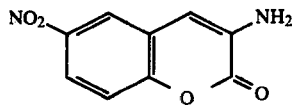

3-Amino-6-nitrocoumarin

A solution of N-(6-nitro-2-oxo-2H-1-benzopyran-3-yl)acetamide (7.5 g, 0.03 mole) in concentrated sulfuric acid (60 ml) and glacial acetic acid (60 ml) is heated at 90° C. for 30 minutes. The reaction mixture is cooled and poured over ice. The product is filtered off and recrystallized from ethyl acetate-methanol to give white crystals (4.7 g, 75%), mp. 173–174.

Anal. Calcd. for C₉H₆N₂O₄: C, 52.43; H, 2.93; N, 13.59. Found: C, 52.53; H, 3.03; N, 13.25.

L. Reppel and W. Schmollack, *Arch. Pharm.* 296, 365–99 (1963)

EXAMPLE 9

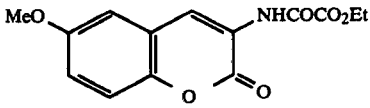

Acetic acid, [(6-methoxy-2-oxo-2H-1-benzopyran-3-yl)amino]oxo-,ethyl ester

A mixture of 3-amino-6-methoxycoumarin (3.2 g, 0.017 mole), ethyl oxalyl chloride (2.73 g, 0.02 mole) and pyridine (3.12 g, 0.04 mole) in methylene chloride (20 ml) is stirred at room temperature for 2 hours. The solvent is removed under reduced pressure to give a solid residue. The residue is triturated with water, filtered and dried. Recrystallization from ethyl acetate gives white crystals (4.0 g, 82%). mp. 147–150.

Anal. Calcd. for C₁₄H₁₃NO₆: C, 57.73; H, 4.50; N, 4.82. Found: C, 57.68; H, 4.47; N, 4.75.

EXAMPLE 10

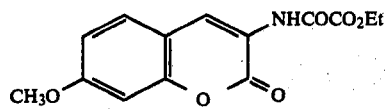

Acetic acid, [(7-methoxy-2-oxo-2H-1-benzopyran-3-yl)amino]oxo-,ethyl ester

Prepared by the method described for example 9 from 3-amino-7-methoxycoumarin (3.82 g, 0.02 mole). Recrystallization from ethyl acetate gives off-white crystals (5.5 g, 94%), mp. 196–197.

Anal. Calcd. for C₁₄H₁₃NO₆: C, 57.73; H, 4.50; N, 4.82. Found: C, 57.87; H, 4.80; H, 4.80.

This compound was tested in accordance with the PCA Test, in which at 5 mg/kg there was 19% inhibition.

EXAMPLE 11

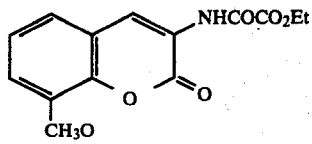

Acetic acid, [(8-methoxy-2-oxo-2H-1-benzopyran-3-yl)amino]oxo-,ethyl ester

Prepared by the method described for example 9 from 3-amino-8-methoxycoumarin (3.82 g, 0.02 mole). Recrystallization from ethyl acetate gives white crystals (5.3 g, 91%), mp. 180–181.

Anal. Calcd. for C₁₄H₁₃NO₆: C, 57.73; H, 4.50; N, 4.82. Found: C, 57.75; H, 4.52; N, 4.92.

This compound was tested in accordance with the PCA Test, in which at 5 mg/kg there was 71% inhibition.

EXAMPLE 12

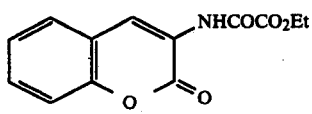

Ethyl (2-oxo-2H-1-benzopyran-3-yl)aminooxoacetate

Prepared by the method described for example 9 from 3-aminocoumarin (12.0 g, 0.075 mole). Recrystallization from ethanol gives white crystals (16 g, 82%) mp. 156–158.

Anal. Calcd. for C₁₃H₁₁NO₅: C, 59.77; H, 4.24; N, 5.36. Found: C, 59.55, H, 4.28; N, 5.34.

This compound was tested in accordance with the PCA Test, in which at 5 mg/kg there was 18% inhibition.

EXAMPLE 13

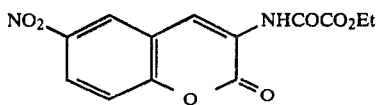

Acetic acid,
[(6-nitro-2-oxo-2H-1-benzopyran-3-yl)amino]oxo-,ethyl ester

Prepared by the method described for example 9 from 3-amino-6-nitrocoumarin (1.82 g, 0.009 mole). Recrystallization from ethyl acetate gives white crystals (1.33 g, 49%), mp. 227–229.

Anal. Calcd. for $C_{13}H_{10}N_2O_7$: C, 50.98; H, 3.29; N, 9.15. Found: C, 51.02; H, 3.56; N, 9.35.

EXAMPLE 14

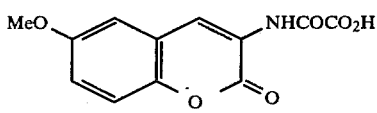

Acetic acid,
[(6-methoxy-2-oxo-2H-1-benzopyran-3-yl)amino]oxo

Ethyl (6-methoxy-2-oxo-2H-1-benzopyran-3-yl)aminooxoacetate (3.2 g) is suspended in ethanol (75 ml) and water (75 ml). 0.1 N sodium hydroxide solution is added dropwise, with occasional warming on a steam bath, until the reaction mixture remained slightly basic. The solution is acidified with 5 N hydrochloric acid and stirred at room temperature for 30 minutes. The product is filtered off and washed with water. Recrystallization from dimethylformamide gives white crystals (2.24 g, 78%) mp. 212–215.

Anal. Calcd. for $C_{12}H_9NO_6$: C, 54.76; H, 3.45; N, 5.32. Found: C, 54.67; H, 3.91; N, 6.10.

This compound was tested in accordance with the PCA Test, in which at 5 mg/kg there was 15% inhibition.

EXAMPLE 15

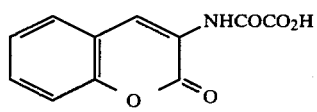

(2-oxo-2H-1-benzopyran-3-yl)aminooxoacetic acid

Prepared by the method described for example 14 from ethyl (2-oxo-2H-1-benzopyran-3-yl)aminooxoacetate (2.0 g). Recrystallization from ethanol-methylene chloride gives white crystals (1.48 g, 83%) mp. 217–219.

Anal. Calcd. for $C_{11}H_7NO_5$: C, 56.66; H, 3.03; N, 6.01. Found: C, 56.77; H, 3.09; N, 5.88.

This compound was tested in accordance with the PCA Test, in which at 5 mg/kg there was 100% inhibition.

EXAMPLE 16

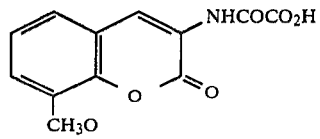

Acetic acid,
[(8-methoxy-2-oxo-2H-1-benzopyran-3-yl)amino]oxo

Prepared by the method described for example 14 from ethyl (8-methoxy-2-oxo-2H-1-benzopyran-3-yl)aminooxoacetate (2.0 g). Recrystallization from dimethylformamide gives white crystals (1.3 g, 72%) mp. 222–223.

Anal. Calcd. for $C_{12}H_9NO_6$: C, 54.76; H, 3.45; N, 5.32. Found: C, 54.49; H, 3.48; N, 5.25.

This compound was tested in accordance with the PCA Test, in which at 5 mg/kg there was 100% inhibition.

EXAMPLE 17

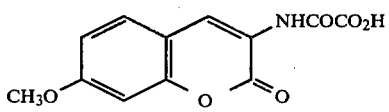

Acetic acid,
[(7-methoxy-2-oxo-2H-1-benzopyran-3-yl)amino]oxo

Prepared by the method described for example 14 from ethyl (7-methoxy-2-oxo-2H-1-benzopyran-3-yl)aminooxoacetate (3.0 g). Recrystallization from dimethylformamide gives white crystals (2.6 g, 96%), mp. 232–233.

Anal. Calcd. for $C_{12}H_9NO_6$: C, 54.76; H, 3.45; N, 5.32. Found: C, 54.52; H, 3.64; N, 5.37.

This compound was tested in accordance with the PCA Test, in which at 5 mg/kg there was 100% inhibition.

EXAMPLE 18

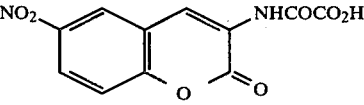

Acetic acid,
[(6-nitro-2-oxo-2H-1-benzopyran-3-yl)amino]oxo

Prepared by the method described for example 14 from ethyl (6-nitro-2-oxo-2H-1-benzopyran-3-yl)aminooxoacetate (1.0 g). Recrystallization from dimethylformamide gives white crystals (0.7 g, 77%), mp. 235–236.

Anal. Calcd. for $C_{11}H_6N_2O_7$: C, 47.49; H, 2.17; N, 10.07. Found: C, 47.33; H, 2.31; N, 10.30.

This compound was tested in accordance with the PCA Test, in which at 5 mg/kg there was 38% inhibition.

We claim:

1. A compound of the formula:

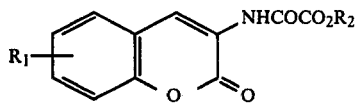

wherein $R_1$ is hydrogen, halogen, hydroxy, lower alkoxy, lower alkyl or nitro and $R_2$ is hydrogen or lower alkyl and their pharmaceutically acceptable salts thereof.

2. A compound according to claim 1 which is Acetic acid, [(6-methoxy-2-oxo-2H-1-benzopyran-3-yl)amino]oxo-,ethyl ester.

3. A compound according to claim 1 which is Acetic acid, [(7-methoxy-2-oxo-2H-1-benzopyran-3-yl)amino]oxo-,ethyl ester.

4. A compound according to claim 1 which is Acetic acid, [(8-methoxy-2-oxo-2H-1-benzopyran-3-yl)amino]oxo-,ethyl ester.

5. A compound according to claim 1 which is Ethyl (2-oxo-2H-1-benzopyran-3-yl)aminooxoacetate.

6. A compound according to claim 1 which is Acetic acid, [(6-nitro-2-oxo-2H-1-benzopyran-3-yl)amino]oxo-,ethyl ester.

7. A compound according to claim 1 which is Acetic acid, [(6-methoxy-2-oxo-2H-1-benzopyran-3-yl)amino]oxo.

8. A compound according to claim 1 which is (2-oxo-2H-1-benzopyran-3-yl)aminooxoacetic acid.

9. A compound according to claim 1 which is Acetic acid, [(8-methoxy-2-oxo-2H-1-benzopyran-3-yl)amino]oxo.

10. A compound according to claim 1 which is Acetic acid, [(7-methoxy-2-oxo-2H-1-benzopyran-3-yl)amino]oxo.

11. A compound according to claim 1 which is Acetic acid, [(6-nitro-2-oxo-2H-1-benzopyran-3-yl)amino]oxo.

* * * * *